United States Patent [19]

Podlech

[11] Patent Number: 4,729,235

[45] Date of Patent: Mar. 8, 1988

[54] TEST PIECE FOR INSPECTION BY ULTRASONIC METHOD

[75] Inventor: Manfred Podlech, Hebertshausen, Fed. Rep. of Germany

[73] Assignee: MTU Motoren- und Turbinen- Union München GmbH, Munich, Fed. Rep. of Germany

[21] Appl. No.: 9,594

[22] Filed: Jan. 29, 1987

Related U.S. Application Data

[63] Continuation of Ser. No. 802,362, Nov. 27, 1985, abandoned.

[30] Foreign Application Priority Data

Nov. 30, 1984 [DE] Fed. Rep. of Germany ....... 3443675

[51] Int. Cl.⁴ .............................................. G01C 25/00
[52] U.S. Cl. .................................................. 73/1 DV
[58] Field of Search ............... 73/1 R, 1 DV; 367/13; 29/407; 148/128; 164/4.1

[56] References Cited

U.S. PATENT DOCUMENTS

| 4,173,139 | 11/1979 | Conn | 73/1 DV |
| 4,203,315 | 5/1980 | Vieu et al. | 73/1 R |
| 4,233,720 | 11/1980 | Rozmus | 29/407 |
| 4,309,904 | 1/1982 | Jones et al. | 73/1 DV |
| 4,453,408 | 6/1984 | Clayman | 73/1 DV |

FOREIGN PATENT DOCUMENTS

| 0084989 | 8/1983 | European Pat. Off. | 73/1 DV |
| 0055752 | 6/1983 | Japan . | |
| 0462127 | 10/1973 | U.S.S.R. | 73/1 DV |

OTHER PUBLICATIONS

Conn, "New and Improved ASTM Type Ultrasonic Standard Reference Blocks", Conference, Jun. 1978.
"PM Aerospace Materials", vol. 2, Nov. 12–14, 1984 (not translated).

Primary Examiner—Stewart J. Levy
Assistant Examiner—Robert R. Raevis
Attorney, Agent, or Firm—Barnes & Thornburg

[57] ABSTRACT

A test piece for use in ultrasonic testing of materials or of powdered metallurgically manufactured workpieces to witness minute flaws, in which reference flaws are incorporated in at least one surface of the test piece or in the joint zone between test piece sections.

19 Claims, 1 Drawing Figure

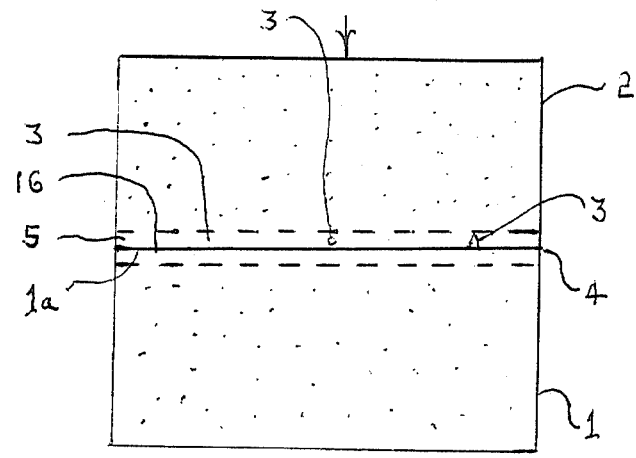

TEST PIECE FOR INSPECTION BY ULTRASONIC METHOD

This is a file wrapper continuation of application Ser. No. 802,362, filed Nov. 27, 1985, now abandoned.

This invention relates to a test piece for inspection by the ultrasonic method using reference flaws and/or reference reflectors, especially for verifying the accuracy of or calibrating high-resolution ultrasonic test units, whereby the test piece is split and the artificial flaw is adapted to be incorporated into the joining zone of the parting surfaces rejoined by especially the diffusion process.

For testing test units or for calibrating an ultrasonic test unit, use has already been made of reference flaws taking the shape of holes or bores, such as cross or bottom bores. The size of such holes or recesses, however, was too large to product suitable reference flaws for use in ultrasonic inspection for purposes of material testing, for the flaws to be actually observed in the material (contaminations) are much smaller.

It is the principal object of the present invention to provide a test piece for the ultrasonic inspection which has minute reference flaws, especially smaller than 0.5 mm and in the micrometer range, and which can be used in materials testing.

As solution to the underlying problem, it is proposed in connection with a split test piece having partial surfaces of a joining zone connected in particular by diffusion, into which are adapted to be incorporated reference flaws, that the reference flaws/reflectors have a particular shape of a size smaller than 0.5 mm and consist of a material which is made fully or at least superficially conductive/reflective and is incorporated in the joining zone of a test piece made by powder-metallurgical process.

Compared with prior art solid test pieces with particle sizes in the mm-range, the present invention offers the advantage that with test pieces made by powder-metallurgical process, artifical flaws can be incorporated that are smaller—by about a full order of magnitude—than the particle sizes of the usual metallic test pieces. In other words, the reference flaw or reference reflector of the present invention can be made and incorporated in sizes, shapes and orientations that reflect actual conditions. The reference flaws produced by the present invention can readily be recognized by ultrasonic test signals and this greatly improves verification of instrument quality or the calibration of ultrasonic test units or their probes. Appreciably large cavities or recesses between the surfaces of the test pieces are prevented. Nor will the joined members reflect ultrasonic waves at the joining zone. This effect is promoted by the particulate shape of the reference flaws and also by the material selected.

In particular, a diffusion zone in the joint between the surfaces of the test pieces has given excellent results.

The reference flaws with their particulate shape and size can readily be adapted to suit the method of embedding them in their respective recesses.

For use in reference flaws, metal compounds in the shape of regularly or irregularly formed particles have given good results when embedded in or placed on the surface or layer to be joined, while metallic materials or composites using metallic materials and other materials have proved satisfactory for the test piece.

These and other objects, features and advantages of the present invention will become more apparent from the following description when taken in conjunction with the accompanying drawing, which shows, for purposes of illustration only, one embodiment in accordance with this invention, and wherein:

The single FIGURE is a somewhat schematic view of a test piece in accordance with the present invention.

Referring to the single FIGURE, a test piece lower member 1 is joined to a test piece upper member 2 by means of diffusion process. Both members 1 and 2 consist of metallic materials, i.e., metals or metal alloys or composites of metallic bodies with other materials, processed by powder-metallurgical methods, such as, for example, by pressing (CIP, HIP) or sintering. Specifically suitable materials are:

API, "Astroloy Powder" TM manufactured by Henry Wigging Alloys, Ltd., England. A high temperature nickel-base alloy with a relative low C-content (low C astroloy)

AF115, high temperature nickel-base alloy manufactured upon request of General Electric (USA) in the Air Force Laboratories IN 100, "Inconel" TM manufactured by Inco Alloys International, Inc. U.S.A.

The shape of the test piece is matched to the specific properties of the component to be tested; for example, with powder-metallurgical parts, the preferred depths of flaws are 2 to 10 mm in 1-mm increments.

The test flaws 3 within the joining zone between members 1 and 2 are constituted by conductive/reflective particles having a size of about 1 mm–0.5 mm.

The preparation of the test piece is as follows:

Before the members are joined, a recess is produced in the surface 1a, for example, of the test piece lower member 1 and/or in the surface 1b of the test piece upper member 2 which has a size corresponding to the approximate size of the test flaw. The recess may be produced physically or chemically, preferably electrochemically, or by electrolytic removal or by an imprint with a hardness ball or other tester of specific depth and shape. A material of known shape, size and material properties (e.g. zirconium oxide, silicon dioxide, alumina ($Al_2O_3$), diamond, graphite) such as spheres, grains or other regularly or irregularly shaped particles, is then embedded in the depression or recess.

Sufficiently hard materials can be placed directly on the surface, obviating the need for a recess. When a bond layer 5 is used, it is intended to cover the particles. The bond layer may for example, be a nickel base layer.

The preferred joining method is diffusion bonding, more particularly diffusion welding. This provides the advantage that the joint zone 4 exhibits composite material properties and will not produce a separate indication in ultrasonic testing.

After bonding, the diffusion zone contains test flaws, the location, size, form and material of which are exactly known, so that they are ideally suited as points of reference for the conventional setting, calibration, and verification of the ultrasonic testing method or equipment. The particular material used for the test flaw should be selected to contrast with the properties of the test piece.

The test piece of the present invention has proved valuable, especially with ultrasonic testing of the powder-metallurgical materials and workpieces made therefrom, where it recognized minute flaws with a high degree of reflection.

For joining the test pieces, use can be made also of joining methods other than described above, such as facing (e.g. by rolling or explosive process) or the deposition of layers (vapor deposition, cathode sputtering or galvanic process). The materials of the test piece used can also be different from those described hereinabove, as long as they admit of ultrasonic inspection. This applies equally to the pieces or particles that are embedded in the recesses or depressions of the test piece to serve for reference, or that are placed therebetween. Suitable also would be some other metal or compound, metal-ceramic compounds or glass-metal compounds, especially materials that are good conductors.

Such materials are commercially available in the form of grainy powder or spheres or granulate in suitable sizes and compositions.

Suitable also would be particles or pieces such as grains, spheres, granulate and the like that were coated for surface conductivity or reflection.

Apart from its use in ultrasonic testing, the test piece, if given suitable contrast, will be useful also in optical inspection methods.

In the ultrasonic inspection of materials, use is made of the usual frequency ranges and wave lengths. The preferred beam direction (arrowhead) is normal to the joint zone (surface).

The ultrasonic transmitter and/or probe and the test piece should be adapted to suit one another in shape and in size.

While I have shown and described only one embodiment in connection with the present invention, it is understood that the same is not limited thereto but is susceptible of numerous changes and modifications as known to those skilled in the art, and I therefore do not wish to be limited to the details shown and described herein but intend to cover all such changes and modifications as are encompassed by the scope of the appended claims.

I claim:

1. A split powdered metallurgically manufactured test piece for ultrasonic inspection including at least one artificial flaw means therein for testing instrument quality or for calibrating high-resolution ultrasonic test units, comprising surface means in the split powdered metallurgically manufactured test piece defining a joining zone between said surface means, artificial flaw means incorporated between the surface means of the joining zone, the artificial flaw means having a particulate shape of a size smaller than 0.5 mm in its largest dimension and incorporated in the joining zone of the split provided metallurgically manufactured test piece.

2. A test piece according to claim 1, wherein the artificial flaw means is incorporated in a diffusion zone of a laminate joint of the split test piece.

3. A test piece according to claim 2, wherein the artificial flaw means is matched to the depth and shape of a recess means produced for the purpose of incorporating the artificial flaw means.

4. A test piece according to claim 3, wherein the artificial flaw means are made of a material selected to contrast with the properties of the test piece.

5. A test piece according to claim 4, wherein the artificial flaw means is made from a material selected from the group consisting of metals, metal alloys and composites of metals with other materials.

6. A test piece according to claim 5, wherein the artificial flaw means are made of metal compounds.

7. A test piece according to claim 5, wherein the artificial flaw means form at least one of reference flaws and reference reflectors.

8. A test piece according to claim 7, wherein the artificial flaw means constitute reference flaws and reference reflectors.

9. A test piece according to claim 5, wherein the surface means are joined by a diffusion method.

10. A test piece according to claim 1, wherein the material of the artificial flaw means is fully conductive or reflective.

11. A test piece according to claim 1, wherein the artificial flaw means is matched to the depth and shape of a recess means produced for the purpose of incorporating the artificial flaw means.

12. A test piece according to claim 1, wherein the artificial flaw means are made of a material subject to contract with the properties of the test piece.

13. A test piece according to claim 1, wherein the artificial flaw means is made from a material selected from the group consisting of metals, metal alloys and composites of metals with other materials.

14. A test piece according to claim 1, wherein the artificial flaw means are made of metal compounds.

15. A test piece according to claim 1, wherein the artificial flaw means form at least one of reference flaws and reference reflectors.

16. A test piece according to claim 1, wherein the artificial flaw means constitute reference flaws and reference reflectors.

17. A test piece according to claim 1, wherein the surface means are joined by a diffusion method.

18. A test piece according to claim 17, wherein the material of the artificial flaw means is fully conductive or reflective.

19. A test piece according to claim 1, wherein the powdered metallurgically manufactured test piece has no particles therein which are equal to or greater than the size of the artificial flaw means.

* * * * *